US009492190B2

(12) United States Patent
Brannan et al.

(10) Patent No.: US 9,492,190 B2
(45) Date of Patent: Nov. 15, 2016

(54) TISSUE DISSECTORS (75) Inventors: Joseph D. Brannan, Erie, CO (US);
Kaylen J. Haley, Westminster, CO (US); Casey M. Ladtkow, Westminster, CO (US); Richard A. Willyard, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 1314 days.

(21) Appl. No.: 13/024,041

(22) Filed: Feb. 9, 2011

(65) Prior Publication Data
US 2012/0203220 A1 Aug. 9, 2012

(51) Int. Cl.
*A61B 18/18* (2006.01)
*A61B 17/32* (2006.01)
*A61B 17/22* (2006.01)
*A61B 17/34* (2006.01)

(52) U.S. Cl.
CPC ............... *A61B 17/320016* (2013.01); *A61B 2017/22074* (2013.01); *A61B 2017/320048* (2013.01); *A61B 2017/347* (2013.01)

(58) Field of Classification Search
CPC ............ A61B 2017/320048; A61B 5/6853; A61B 2017/347
USPC .......................................... 606/41, 190–197
See application file for complete search history.

(56) References Cited

U.S. PATENT DOCUMENTS

| D223,367 S | 4/1972 | Kountz |
| D263,020 S | 2/1982 | Rau, III |
| D266,842 S | 11/1982 | Villers et al. |
| D278,306 S | 4/1985 | McIntosh |
| 4,552,127 A | 11/1985 | Schiff |
| D295,893 S | 5/1988 | Sharkany et al. |
| D295,894 S | 5/1988 | Sharkany et al. |
| 4,927,413 A | 5/1990 | Hess |
| 5,035,694 A | 7/1991 | Kasprzyk et al. |
| 5,057,106 A | 10/1991 | Kasevich et al. |
| 5,100,388 A | 3/1992 | Behl et al. |

(Continued)

FOREIGN PATENT DOCUMENTS

| CN | 1103807 | 6/1995 |
| DE | 390937 | 3/1924 |

(Continued)

OTHER PUBLICATIONS

European Search Report for European Application No. 12000336.3 dated May 4, 2012.

(Continued)

*Primary Examiner* — Jocelyn D Ram (57) ABSTRACT

A tissue dissector is provided. The tissue dissector includes a cannula and an introducer coaxially coupled to the cannula and movable therein from a retracted position to an extended position. An introducer is coaxially coupleable to the cannula and movable therein from a retracted position to an extended position. The introducer including a generally annular lumen disposed in fluid communication with an inflation port operably disposed on the introducer and in fluid communication with an inflatable balloon that couples to the introducer. The inflatable balloon is movable from a deflated condition for positioning the introducer adjacent target tissue, to an inflated condition for separating the target tissue from nearby tissue and for providing a barrier therebetween such that the nearby tissue is not affected during the electrosurgical procedure.

15 Claims, 4 Drawing Sheets

(56) References Cited

U.S. PATENT DOCUMENTS

| | | | |
|---|---|---|---|
| 5,103,804 A | 4/1992 | Abele et al. | |
| 5,183,463 A | 2/1993 | Debbas | |
| 5,301,682 A | 4/1994 | Debbas | |
| 5,308,354 A * | 5/1994 | Zacca et al. | 606/159 |
| 5,334,187 A * | 8/1994 | Fischell et al. | 604/102.02 |
| D354,218 S | 1/1995 | Van de Peer | |
| 5,383,889 A * | 1/1995 | Warner et al. | 606/192 |
| 5,542,936 A * | 8/1996 | Razi | 604/264 |
| 5,634,928 A | 6/1997 | Fischell | |
| 5,634,935 A | 6/1997 | Taheri | |
| 5,725,545 A * | 3/1998 | Bircoll | A61M 29/02 604/96.01 |
| 5,800,486 A | 9/1998 | Thome et al. | |
| 5,868,775 A * | 2/1999 | Bircoll | A61M 29/02 600/207 |
| D424,693 S | 5/2000 | Pruter | |
| D424,694 S | 5/2000 | Tetzlaff et al. | |
| D425,201 S | 5/2000 | Tetzlaff et al. | |
| 6,092,528 A | 7/2000 | Edwards | |
| 6,117,101 A | 9/2000 | Diederich et al. | |
| 6,277,083 B1 | 8/2001 | Eggers et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,496,737 B2 | 12/2002 | Rudie et al. | |
| 6,514,249 B1 | 2/2003 | Maguire et al. | |
| 6,547,788 B1 * | 4/2003 | Maguire et al. | 606/41 |
| 6,599,288 B2 | 7/2003 | Maguire et al. | |
| 6,652,515 B1 | 11/2003 | Maguire et al. | |
| D487,039 S | 2/2004 | Webster et al. | |
| D496,997 S | 10/2004 | Dycus et al. | |
| D499,181 S | 11/2004 | Dycus et al. | |
| 6,847,848 B2 | 1/2005 | Sterzer et al. | |
| 6,869,431 B2 | 3/2005 | Maguire et al. | |
| 6,997,925 B2 | 2/2006 | Maguire et al. | |
| D525,361 S | 7/2006 | Hushka | |
| 7,089,063 B2 | 8/2006 | Lesh et al. | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,326,201 B2 | 2/2008 | Fjield et al. | |
| D564,662 S | 3/2008 | Moses et al. | |
| 7,410,486 B2 | 8/2008 | Fuimaono et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,826,904 B2 | 11/2010 | Appling et al. | |
| D634,010 S | 3/2011 | DeCarlo | |
| 8,728,081 B2 * | 5/2014 | Lauchner et al. | 606/86 R |
| 8,926,602 B2 * | 1/2015 | Pageard | 606/21 |
| 2003/0028210 A1 * | 2/2003 | Boyle et al. | 606/192 |
| 2003/0060813 A1 | 3/2003 | Loeb et al. | |
| 2003/0178032 A1 * | 9/2003 | Ingle et al. | 128/898 |
| 2004/0148004 A1 * | 7/2004 | Wallsten | 623/1.11 |
| 2005/0038419 A9 | 2/2005 | Arnold et al. | |
| 2005/0080474 A1 | 4/2005 | Andreas | |
| 2006/0229700 A1 | 10/2006 | Acosta | |
| 2006/0271036 A1 | 11/2006 | Garabedian et al. | |
| 2007/0010846 A1 * | 1/2007 | Leung | A61B 17/3478 606/192 |
| 2007/0149963 A1 | 6/2007 | Matsukuma et al. | |
| 2007/0185554 A1 | 8/2007 | Appling et al. | |
| 2008/0086166 A1 * | 4/2008 | Ravikumar | 606/192 |
| 2008/0177369 A1 | 7/2008 | Will | |
| 2009/0048623 A1 * | 2/2009 | Lafosse | A61B 17/0218 606/192 |
| 2009/0062871 A1 | 3/2009 | Chin et al. | |
| 2009/0105745 A1 * | 4/2009 | Culbert | A61B 17/3417 606/192 |
| 2009/0287203 A1 * | 11/2009 | Mazzone et al. | 606/21 |
| 2010/0010303 A1 * | 1/2010 | Bakos | A61B 1/00082 600/115 |
| 2010/0100091 A1 | 4/2010 | Truckai | |
| 2010/0100094 A1 | 4/2010 | Truckai | |
| 2011/0022044 A1 * | 1/2011 | Garabedian et al. | 606/41 |
| 2012/0197319 A1 * | 8/2012 | Auyoung | A61B 17/7097 606/86 R |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | H07503623 A | 4/1995 |
| JP | 07265328 | 10/1995 |
| JP | 08056955 | 3/1996 |
| JP | 08252263 | 10/1996 |
| JP | 09000492 | 1/1997 |

(56) References Cited

FOREIGN PATENT DOCUMENTS

| | | |
|---|---|---|
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2005253916 A | 9/2005 |
| JP | 2008142467 | 6/2008 |
| SU | 166452 | 11/1964 |
| SU | 401367 | 11/1974 |
| SU | 727201 | 4/1980 |
| WO | WO 97/43971 | 11/1997 |
| WO | WO 97/48450 | 12/1997 |
| WO | WO 02069862 | 9/2002 |
| WO | WO2010/035831 | 4/2010 |

OTHER PUBLICATIONS

U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Cams et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.

(56) References Cited

OTHER PUBLICATIONS

Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. Ml, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman et al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
"MDTECH product literature (Mar. 2000) I'D Wire": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AIR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Theroradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 19(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.

(56) References Cited

OTHER PUBLICATIONS

Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.

(56) References Cited

OTHER PUBLICATIONS

European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/USO4/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
Japanese Office Action issued in Applicaiton No. JP 2012-011039 dated Sep. 1, 2015.
Chinese Office Action, with English language translation, issued Jan. 5, 2016 in Application No. CN 201210263892.5.

* cited by examiner

TISSUE DISSECTORS

BACKGROUND

1. Technical Field

The present disclosure relates to tissue dissectors and, more particularly, to percutaneously deployable tissue dissectors including an inflatable balloon at a distal end thereof configured to protect critical tissue structures.

2. Background of Related Art

During an electrosurgical procedure, e.g., a thermal ablation procedure, target tissue is heated to high temperatures, e.g., temperatures high enough to ablate tissue. Under certain surgical environments, it is sometimes necessary to protect critical tissue structures, e.g., organ, bone matter, etc. adjacent the target tissue from the heat associated with the thermal ablation procedure. To protect adjacent tissue, the adjacent tissue is typically dissected, covered, shielded or otherwise treated.

For example, one technique that is commonly utilized for protecting adjacent tissue structure during a thermal ablation procedure includes dissecting adjacent tissue by injecting a fluid, e.g., saline, CO2, D5W, etc., into a space between target tissue and the adjacent tissue. While this technique works well under certain surgical environments, this technique is limited, however, due to the difficulties in controlling the location of the fluid and difficulty in removing all the fluid from the body. In addition, and in the instance where the fluid is a gas, e.g., CO2, the CO2 often dissolves into the tissue, which requires the CO2 to be replenished (sometimes quite frequently) during a surgical procedure. As can be appreciated, having to replenish the CO2 during a surgical procedure may increase the length of time needed to effectively perform the surgical procedure.

SUMMARY

The present disclosure provides a tissue dissector configured for use during an electrosurgical procedure. The tissue dissector includes a cannula having a longitudinal channel with a longitudinal axis defined therethrough. The cannula has a notch defined along a length thereof. An introducer is coaxially coupleable to the cannula and movable therein from a retracted position to an extended position. The introducer including a generally annular lumen disposed in fluid communication with an inflation port operably disposed on the introducer and in fluid communication with an inflatable balloon that couples to the introducer. The inflatable balloon is movable from a deflated condition for positioning the introducer adjacent target tissue, to an inflated condition for separating the target tissue from nearby tissue and for providing a barrier therebetween such that the nearby tissue is not critically affected during the electrosurgical procedure.

The present disclosure provides a system for performing an electrosurgical procedure. The system includes a source of electrosurgical energy, an electrosurgical instrument that is adapted to operably couple to the source of electrosurgical energy and configured to electrosurgically treat tissue of interest and a tissue dissector. The tissue dissector includes a cannula having a longitudinal channel with a longitudinal axis defined therethrough. The cannula has a notch defined along a length thereof. An introducer is coaxially coupleable to the cannula and movable therein from a retracted position to an extended position. The introducer including a generally annular lumen disposed in fluid communication with an inflation port operably disposed on the introducer and in fluid communication with an inflatable balloon that couples to the introducer. The inflatable balloon is movable from a deflated condition for positioning the introducer adjacent target tissue, to an inflated condition for separating the target tissue from nearby tissue and for providing a barrier therebetween such that the nearby tissue is not critically affected during the electrosurgical procedure.

The present disclosure also provides a method for electrosurgically treating tissue. A step of the method includes positioning an introducer of a tissue dissector adjacent target tissue. Deploying a shaft from the introducer between the target tissue and nearby tissue is a step of the method. The method includes inflating an expandable balloon operably coupled to the introducer such that the nearby tissue separates from the target tissue. The expandable balloon may be segmented into two or more chambers that are sealed from one another by a divider membrane extending along the elongated shaft of the introducer. And electrosurgically treating the target tissue is a step of the method.

BRIEF DESCRIPTION OF THE DRAWINGS

Embodiments of the presently disclosed tissue dissectors are described hereinbelow with reference to the drawings wherein.

DETAILED DESCRIPTION OF THE EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end of a surgical instrument that is closer to the user, while the term "distal" will refer to an end of a surgical instrument that is farther from the user.

Figure 1:
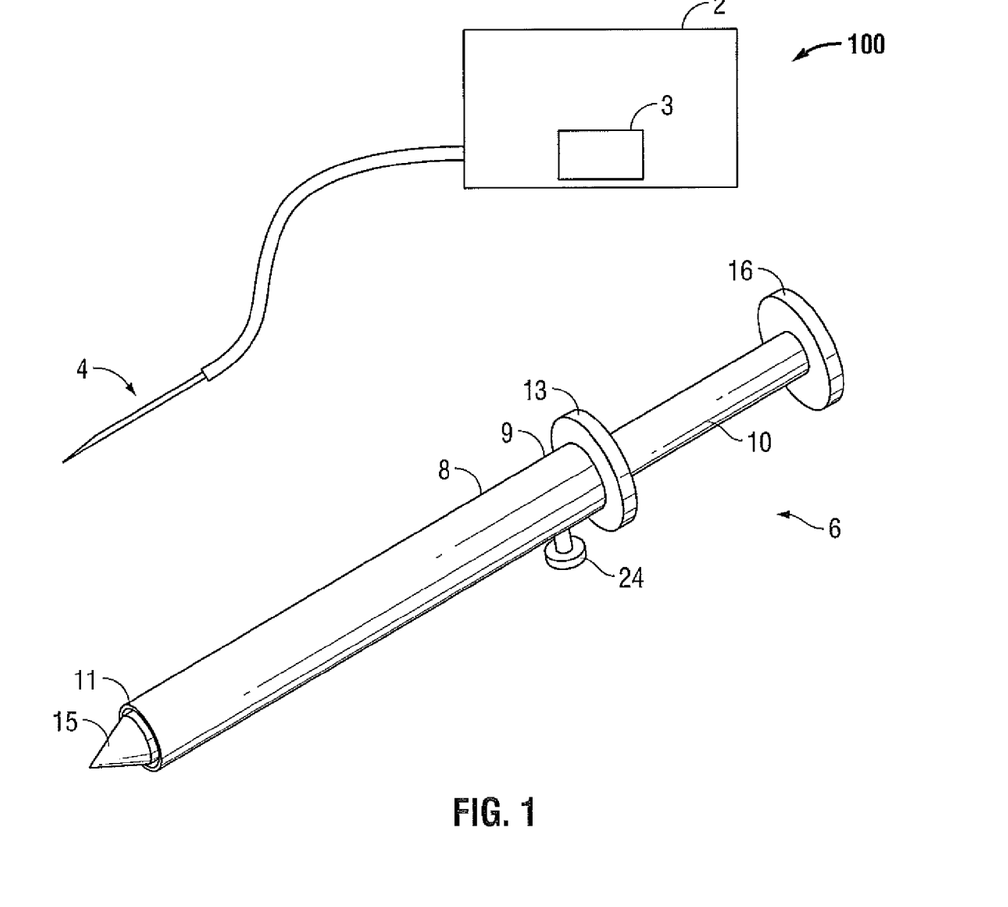
FIG. 1 is a schematic view of a system for performing an electrosurgical procedure according to an embodiment of the present disclosure.

Referring to FIG. 1, a system 100 for electrosurgically treating tissue is illustrated including a source of electrosurgical energy, e.g., an electrosurgical generator 2, an electrosurgical instrument, e.g., a microwave antenna assembly 4, a fluid source 3 and a tissue dissector 6. The system 100 may be configured to perform one or more electrosurgical procedures for treating tissue including, but not limited to, ablating, coagulating, and fulgurating tissue. For purposes herein, the system 100 is described in terms of tissue ablation.

With continued reference to FIG. 1, electrosurgical generator 2 is configured to generate electrosurgical energy suitable for ablating tissue. Microwave antenna assembly 4 is adapted to operably couple to the electrosurgical generator 2 and is configured to electrosurgically treat tissue of interest (hereinafter referred to as target tissue "T"). Examples of an electrosurgical generator 2 and microwave antenna assembly 4 are detailed in commonly-owned patent application Ser. No. 12/606,767 to Brannan, filed on Oct. 27, 2009.

Figure 2:
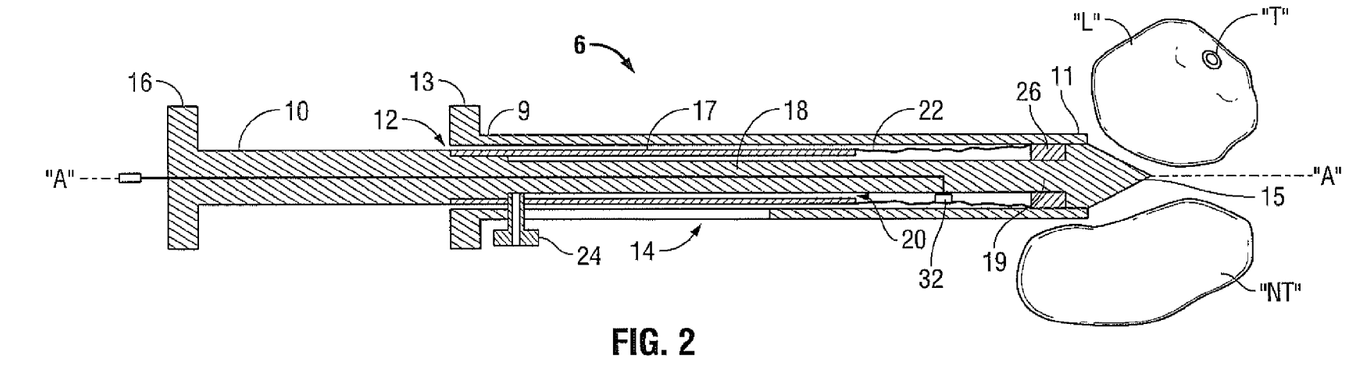
FIG. 2 is a cross-sectional view of a tissue dissector configured for use with the system depicted in FIG. 1.
Figure 3:
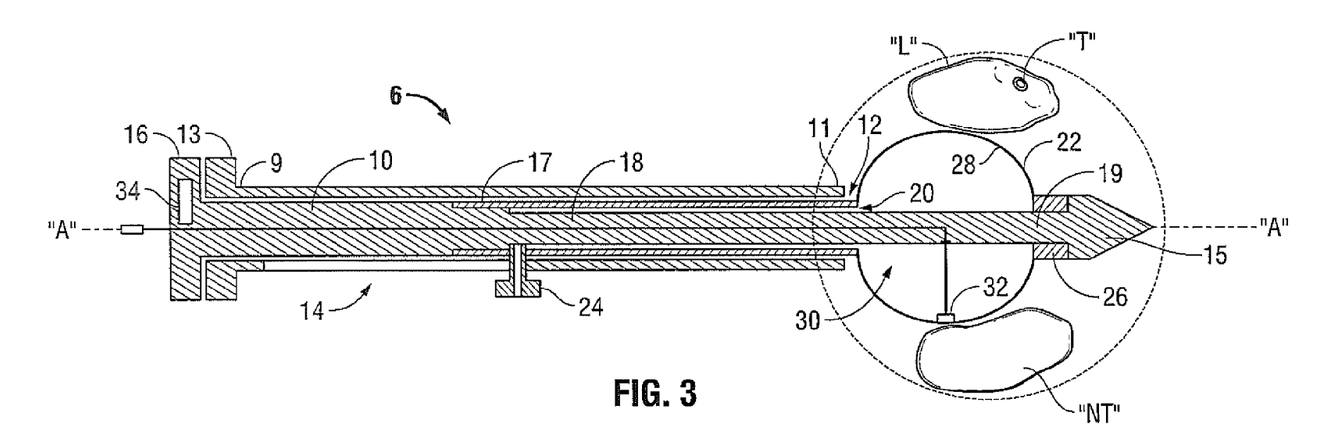
FIG. 3 is a cross-sectional view of the tissue dissector depicted in FIG. 2 with an introducer in a deployed state.

Continuing with reference to FIG. 1, and with reference to FIGS. 2 and 3, an embodiment of the tissue dissector 6 is shown including a cannula 8 and an introducer 10. Cannula 8 (and operative components associated therewith) may be made from any suitable material including but not limited to plastic, surgical steel, etc. In the illustrated embodiment, cannula 8 is made from stainless steel.

Cannula 8 includes open proximal and distal ends 9 and 11, respectively (FIGS. 2 and 3). Open proximal end 9 is of suitable configuration to facilitate translation of the introducer 10 within the cannula 8 (FIG. 2). A flange 13 is disposed adjacent the proximal end 9 of the cannula 8 and functions as a handle for sliding the cannula 8 with respect to the introducer 10 (FIGS. 2 and 3). In certain embodiments, the flange 13 may include one or more components, e.g., hose clamp or the like (not shown), that serve to lock or otherwise maintain the cannula 8 and introducer 10 in a relatively fixed position with respect to one another.

Distal end 11 is configured to releasably couple to the introducer 10 to facilitate inserting the introducer 10 into tissue. More particularly, distal end 11 "overlaps" (FIG. 2) a distal tip 15 of the introducer 10 such that the distal tip 15 is maintained in a relatively fixed orientation with respect to the cannula 8 and is releasable therefrom when a predetermined pressure is applied to the cannula 8, e.g., flange 13, and/or introducer 10. In the illustrated embodiment, the distal end 11 and distal tip 15 of the introducer 10 releasably couple to one another via a friction-fit or press-fit. Other coupling methods are contemplated.

Cannula 8 includes a longitudinal channel 12 (FIGS. 2-4) having a longitudinal axis "A-A" defined therethrough. The channel 12 is configured to receive the introducer 10 therein (FIG. 2) such that the introducer 10 is movable, e.g., translatable and/or rotatable, therein from a retracted position (FIG. 2) to an extended position (FIG. 3).

A notch 14 (FIGS. 2 and 3) of suitable proportion is operably disposed on the cannula 8. The notch 14 is configured to movably house an inflation port 24 (FIGS. 2 and 3) of the introducer 10 therein, as described in more detail below. That is, the notch 14 allows translation of the inflation port 24 along the longitudinal axis "A-A" such that a distal end 19 including an inflatable balloon 22 of the introducer 10 may be deployed from the cannula 8.

With continued reference to FIGS. 2 and 3, the introducer 10 is illustrated. Introducer 10 (and operative components associated therewith) may be made from any suitable material, including those previously mentioned above. In the illustrated embodiments, a portion of the introducer 10 may be made from stainless steel and a portion of the introducer 10 may be made from plastic, as described in more detail below.

Introducer 10 includes a proximal end 16 that functions as a handle that is maneuverable by a user, e.g., a clinician, such that a user may position the introducer 10 within the lumen 12 of the cannula 8 (FIGS. 2 and 3). The proximal end 16 also serves as a "stop member." That is, the proximal end 16 is configured to limit movement of the introducer 10 past a predetermined distance with respect to the cannula 8. To this end, the proximal end 16 is configured to contact the flange 13 of the cannula 8 (FIG. 3).

Figure 4:
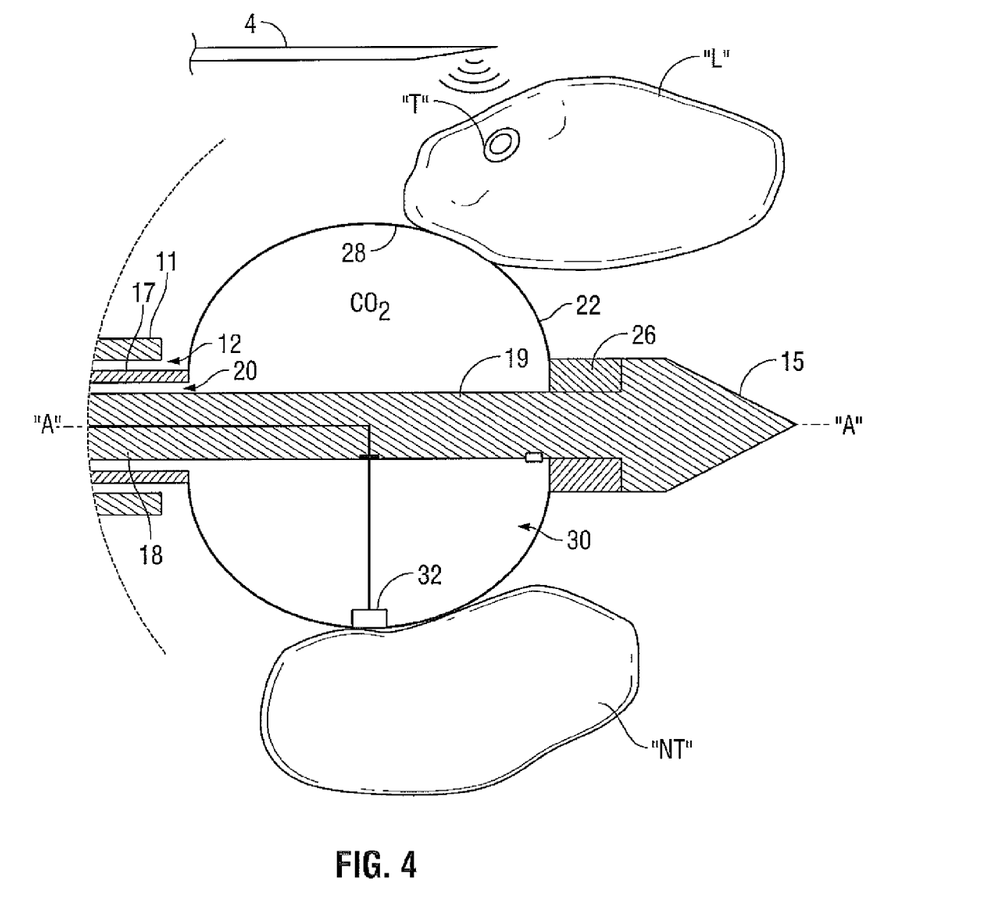
FIG. 4 is an enlarged view of the area of detail depicted in FIG. 3.

The introducer 10 includes a generally elongated configuration. In particular, introducer 10 includes a shaft 18 that extends from the proximal end 16 to the distal end 19, see FIGS. 2 and 3. The introducer 10 includes a generally cylindrical outer member 17 that couples to the shaft 18 adjacent the proximal end 16, see FIGS. 2 and 3. Outer member 17 is disposed around and partially along an elongated shaft 18. Outer member 17 and elongated shaft 18 are positioned about one another to form at least one generally annular lumen 20 therebetween, as best seen in FIG. 4. Outer member 17 may be an integral part of the introducer 10 or, in certain embodiments, outer member 17 may be a separate component coupled to the introducer 10 via one or more suitable coupling devices and/or methods, such as, for example, ultrasonic welding, brazing or the like. Outer member 17 may be made from any suitable material, including those previously mentioned above. In the illustrated embodiment, the outer member 17 is made from plastic, ceramic or metal (FIGS. 2-4).

The annular lumen 20 extends along the length of the outer member 17 to the inflatable balloon 22 (FIGS. 2-4). The annular lumen 20 is configured to receive one or more suitable fluids including gases, e.g., $CO_2$, saline, water, etc. therein. The annular lumen 20 is in fluid communication with the inflation port 24 (FIGS. 2 and 3) and in fluid communication with the inflatable balloon 22, as best seen in FIG. 4.

A generally annular projection in the form of a ring 26 (FIGS. 2-4) is disposed on the elongated shaft 18 and is configured to engage the distal end 11 of the cannula 8 to maintain the introducer 10 in a relatively fixed position as the introducer 10 is positioned adjacent target tissue "T." The ring 26 also serves as a point of fixation for the inflatable balloon 22, as described in more detail below.

Sharpened distal tip 15 is disposed at the distal end 19 adjacent the ring 26 and is configured to pierce tissue to facilitate positioning the tissue dissector 6 adjacent target tissue "T" (FIGS. 2-4). The distal tip 15 may include one or more beveled edges (not shown) that form a relatively sharpened peripheral outer edge. Under certain surgical scenarios, the sharpened distal tip 15 may be configured to temporarily secure to tissue, e.g., bone matter, for maintaining the introducer 10 in a substantially fixed orientation with respect to the cannula 8, such as, for example, when the cannula 8 is being "drawn back" or pulled to deploy the inflatable balloon 22. Alternatively, distal tip 15 may be rounded or dull to prevent unintentional tissue damage as the tissue dissector 6 is being positioned adjacent target tissue.

With reference again to FIGS. 2-4, inflatable balloon 22 is illustrated. Inflatable balloon 22 is configured to protect tissue adjacent or neighboring target tissue, e.g., tissue that is to be electrosurgically treated. More particularly, the inflatable balloon 22 is configured to limit or diminish electrosurgical energy, e.g., microwave field propagation, in addition to thermal conductivity such that neighboring tissue is not critically affected during an electrosurgical procedure. As can be appreciated, this enables aggressive thermal treatment of lesions near a surface of solid organs, e.g., kidney, liver, lungs, etc., with reduced risk of neighboring tissue damage, e.g., bowel, chest wall, abdominal wall, diaphragm, etc.

Inflatable balloon 22 is movable from a deflated condition (FIG. 2) for positioning the introducer 10 adjacent target tissue "T," to an inflated condition (FIGS. 3 and 4) for separating the target tissue "T" from nearby or neighboring tissue "NT" and for providing a barrier therebetween such that the neighboring tissue "NT" is not critically affected during the electrosurgical procedure. (FIGS. 3 and 4), as described in more detail below. In the inflated condition, the inflatable balloon may exhibit one or more suitable shapes, spherical, oval, rectangular, etc. For illustrative purposes, the inflatable balloon 22 is shown having a generally spherical configuration in the expanded configuration (FIGS. 3 and 4). As can be appreciated, the specific shape that the inflatable balloon 22 may exhibit in the inflated condition may vary for a different surgical procedure, the type of tissue that is to be electrosurgically treated, the location of the tissue that is to be treated, a manufacturer's preference, etc.

The inflatable balloon 22 operably couples to the outer member 17 and the ring 26 of the introducer 10 by one or more suitable coupling methods, e.g., ultrasonic welding, soldering, etc (FIGS. 2-4).

Inflatable balloon 22 may be made from any suitable material including but not limited to elastomers, metals or combination thereof. In the embodiment illustrated in FIGS. 1-4, the inflatable balloon 22 is made from a high temperature plastic, e.g., plastic that can withstand temperatures of up to 200° C. In certain embodiments, the inflatable balloon 22 may be made from plastic and have operably coupled thereto one or more conductive materials, described in more detail below.

Inflatable balloon 22 is in fluid communication with the annular lumen 20 and the inflation port 24 such that one or more suitable fluids or gases, e.g., $CO_2$, saline, water, D5W, DI, etc., may be introduced to an interior of the inflatable balloon 22, as best seen in FIG. 4. In the embodiment illustrated in FIGS. 1-4, an interior wall 28 of suitable proportion defines a single reservoir or chamber 30 (FIG. 4) that is configured to be filled with one or more of the previously described fluids, e.g., $CO_2$.

In certain embodiments, the interior wall 28 of the inflatable balloon 22 is configured to support (via one or more suitable coupling methods) one or more temperature sensors or probes 32 thereon (FIGS. 3 and 4). In the illustrated embodiment, the temperature sensor 32 is selected from the group consisting of thermocouples, thermistors and diodes. The temperature sensor 32 is configured to monitor a temperature of the interior wall 28 of the inflatable balloon 22, and therefore monitor temperature of tissue in indirect contact with the interior wall 28. As can be appreciated, this provides an additional level of safety such that an end user may monitor dissected or separated tissue, e.g., neighboring tissue "NT." In the illustrated embodiment, the temperature sensor 32 is operably coupled to an optional audio or visual indicator 34. Moreover, the temperature sensor 32 may be in operative communication with the generator 2 and/or one or more modules, temperature control module (not shown), associated therewith.

Operation of the system 100 is described in terms of use of a method for electrosurgically treating tissue, e.g., a microwave ablation procedure for treating target tissue "T" on a lung "L." The introducer 10 including the distal tip 15, initially, is utilized to pierce tissue such that the introducer 10 may be positioned adjacent target tissue "T," FIG. 2. Subsequently, the inflatable balloon 22 is deployed from the cannula 8 such that the inflatable balloon 22 is between the target tissue "T" and nearby tissue "NT" (FIGS. 3 and 4). The inflatable balloon 22 is inflated with one or more of the aforementioned fluids, for example, $CO_2$, such that the inflatable balloon 22 transitions from the non-inflated state (FIG. 2) to the inflated state (FIGS. 3 and 4). As the inflatable balloon 22 transitions from the non-inflated state to the inflated state, the inflatable balloon 22 separates the nearby tissue "NT" from the target tissue "T". Thereafter, the target tissue "T" is electrosurgically treated via the microwave antenna assembly 4.

As can be appreciated, the tissue dissector 6 disclosed herein effectively separates and isolates the nearby tissue "NT" from the target tissue "T" and reduces and/or eliminates the likelihood of the nearby tissue "NT" being critically affected as the target tissue "T" is electrosurgically treated. This is accomplished without the need of having to introduce any extra fluid to the surgical environment, which, as noted above, may increase the length of time needed to effectively perform the surgical procedure.

Figure 5:
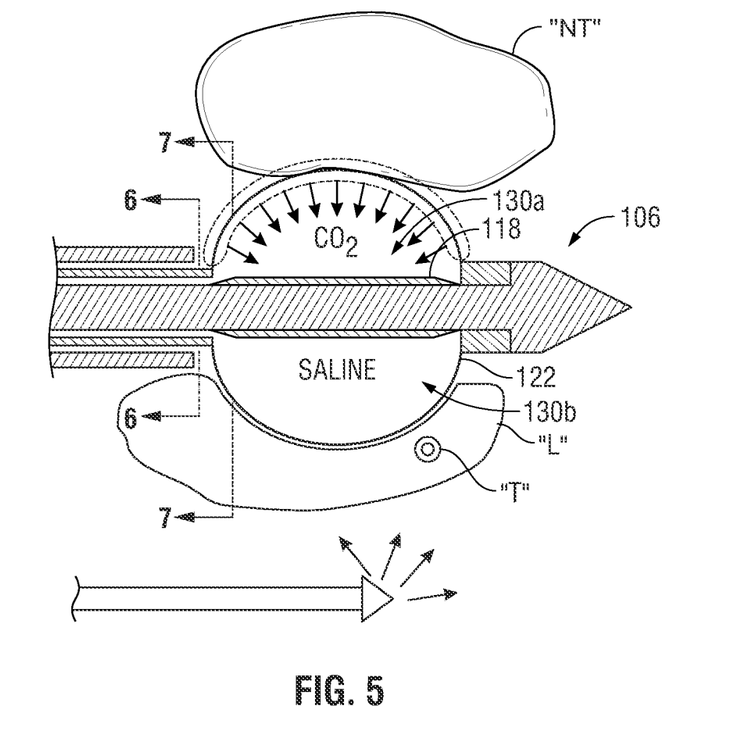
FIG. 5 is a cross-sectional view of a tissue dissector configured for use with the system depicted in FIG. 1 according to another embodiment of the present disclosure.
Figure 6:
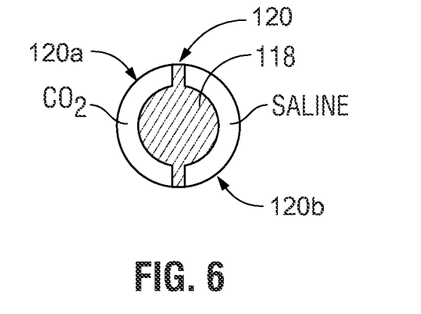
FIG. 6 is a cross-sectional view taken along the line segment 6-6 in FIG. 5.
Figure 7:
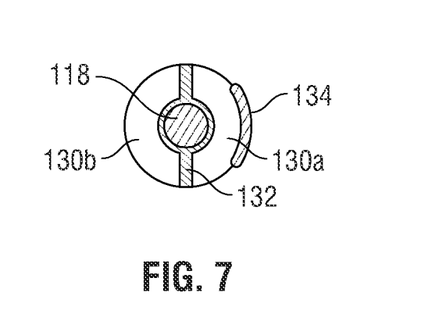
FIG. 7 is a cross-sectional view taken along the line segment 7-7 in FIG. 5.

With reference to FIGS. 5-7, a tissue dissector 106 is illustrated according to another embodiment of the present disclosure. Tissue dissector 106 is substantially similar to the tissue dissector 6. Accordingly, only those features that are unique to tissue dissector 106 are described in detail herein.

An annular lumen 120 defined between an outer member 117 and an elongated shaft 118 includes a split configuration defining two hemispherical lumens 120a and 120b (FIG. 6). Each of the hemispherical lumens 120a and 120b is in fluid communication with an inflation port (not explicitly shown) that is configured to supply each hemispherical lumen 120a and 120b with a corresponding fluid or gas. To this end, the inflation port includes a multivalve configuration having two or more valves that selectively supply fluid or gas to a corresponding one of the hemispherical lumens 120a and 120b. Alternatively, the inflation port may include a lumen pair, i.e., two independent lumens, that are in fluid communication with a respective hemispherical lumen 120a and 120b. In the embodiment illustrated in FIGS. 5-7, the inflation port is configured to supply $CO_2$ to hemispherical lumen 120a and either saline or water to hemispherical lumen 120b (FIG. 6). As can be appreciated, the specific fluid or gas supplied to either of the hemispherical lumens 120a and 120b may vary for a different surgical procedure, the type of tissue that is to be electrosurgically treated, the location of the tissue that is to be treated, a manufacturer's preference, etc.

FIG. 7 illustrates a cross-sectional view of an inflatable balloon 122. Inflatable balloon 122 includes two segmented reservoirs or chambers 130a and 130b that are sealed from one another by a divider membrane 132 that extends along the elongated shaft 118 of the introducer 110. The divider membrane 132 may be made from any suitable material, e.g., an elastomeric material. The divider membrane 132 is configured to provide a fluid-tight seal between the two chambers 130a and 130b such that the respective fluids $CO_2$ and saline do not mix during inflation and deflation of the inflatable balloon 122. The chamber 130a with the $CO_2$ therein is configured to provide thermal insulation from the heated saline in the chamber 130b when the target tissue "T" is heated. Moreover, the chamber 130b with the saline therein provides a medium that allows the electrosurgical energy, e.g., microwave energy, to attenuate rapidly therein when the target tissue "T" is heated.

Unlike inflatable balloon 22, one or more suitable conductive materials, such as, for example, metal, is operably disposed on the inflatable balloon 122. More particularly, a portion or side, e.g., a hemisphere of the inflatable balloon that corresponds to a chamber that is configured to receive the $CO_2$, is made from or configured to operably couple to one or more suitable conductive materials. For example, and in one particular embodiment, a coating of one or more suitable metals 134, e.g., a thin film 134 of copper or stainless steel, conductive polymer, titanium, gold, etc., is disposed on an exterior (or in some instances both an exterior and interior) surface along a side of the inflatable balloon 122 that corresponds to the chamber 130a (FIG. 7). In another embodiment, the conductive material may be disposed on the interior wall of the inflatable balloon 122 that corresponds to the chamber 130a. The conductive metal 134 is configured to reflect a majority of the microwave energy such that the microwave energy does not critically affect neighboring tissue "NT."

In certain instances, it may prove advantageous to coat the divider membrane 132 with a thin metal film or conductive material to achieve the same or similar effect as coating the exterior and/or interior surface of the inflatable balloon 122. In this instance, the $CO_2$ hemisphere provides space, the saline hemisphere attenuates the microwave energy and the divider membrane 132 reflects microwave energy back toward target tissue "T" and away from neighboring tissue "NT."

In use, the chamber 130a, i.e., the chamber that includes the conductive material 134 and, thus, configured to receive the $CO_2$ therein, is positioned adjacent the neighboring tissue "NT" and chamber 130b, i.e., the chamber that is configured to receive the saline therein, is positioned adjacent the target tissue "T," see FIG. 5. Subsequently, each of the chambers 130a and 130b are filled respectively with $CO_2$ and saline to separate target tissue "T" from the neighboring tissue "NT." Thereafter, the target tissue "T" is electrosurgically treated via the microwave antenna assembly 4. The conductive material 134 reflects the microwave energy that is not absorbed or attenuated by the saline in the chamber 130b.

From the foregoing and with reference to the various figure drawings, those skilled in the art will appreciate that certain modifications can also be made to the present disclosure without departing from the scope of the same. For example, in certain embodiments, the inflatable balloons 22/122 may be configured to inflate or "fill" in a specific manner to conform to a specific tissue structure. For example, and in certain instances, the inflatable balloon 22/122 may be configured to have a cupped surface in an inflated configuration that conforms to a shape of a kidney. In certain instances, the inflatable balloon 22/122 may be configured to have a flat or slightly curved surface in an inflated configuration that conforms to a shape of a liver.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue dissector, comprising:
   a cannula having a longitudinal channel defined therethrough, the cannula having a notch defined along a length thereof; and
   an introducer coaxially coupleable to the cannula and movable therein between a retracted position and an extended position, the introducer including:
   an elongated shaft having a distal tip configured to pierce tissue;
   an outer member having a proximal portion connected to the elongated shaft and a distal portion disposed in spaced relation to the elongated shaft to define an annular lumen between the distal portion of the outer member and the elongated shaft, the annular lumen disposed in fluid communication with an inflation port operably disposed on the introducer and in fluid communication with an inflatable balloon, the inflatable balloon configured to couple to the distal portion of the outer member; and
   an annular projection disposed on a distal end of the introducer proximal to the distal tip and configured to be disposed within the longitudinal channel defined through the cannula and to engage a distal end of the longitudinal channel defined through the cannula to maintain the introducer in a fixed position relative to the cannula when the introducer is in the retracted position,
   wherein the inflatable balloon is movable between a deflated condition for positioning the introducer adjacent target tissue, and an inflated condition for separating the target tissue from nearby tissue and for providing a barrier therebetween.

2. The tissue dissector according to claim 1, wherein the annular projection is disposed distal to the inflatable balloon.

3. The tissue dissector according to claim 1, wherein a proximal end of the introducer includes a handle configured to facilitate movement of the introducer relative to the cannula.

4. The tissue dissector according to claim 1, wherein the introducer and the cannula are made from a material selected from the group consisting of plastic and stainless steel.

5. The tissue dissector according to claim 1, wherein the inflation port is positioned within the notch of the cannula.

6. The tissue dissector according to claim 1, wherein at least a portion of the inflatable balloon is made from a material selected from the group consisting of a plastic and a metal.

7. The tissue dissector according to claim 1, wherein at least a portion of the inflatable balloon is made from a plastic and at least a portion of the balloon includes a conductive material.

8. The tissue dissector according to claim 1, further comprising a temperature sensor operably disposed on an interior wall of the inflatable balloon and configured to monitor a temperature of fluid inside the inflatable balloon, the temperature sensor configured to communicate with one of an audio or visual indicator operably disposed on a proximal end of the introducer.

9. The tissue dissector according to claim 1, wherein the inflatable balloon is segmented into at least two chambers that are sealed from one another by a divider membrane extending along the elongated shaft of the introducer.

10. The tissue dissector according to claim 9, wherein at least one of the at least two chambers is configured to receive $CO_2$ and at least one of the at least two chambers is configured to receive one of saline or water.

11. The tissue dissector according to claim 10, wherein the at least one generally annular lumen is further defined by two individual lumens each in fluid communication with a respective one of the at least two chambers of the inflatable balloon.

12. The tissue dissector according to claim 11, wherein the inflation port includes at least one of a multi-valve configuration or a lumen pair configuration, wherein each of the multi-valve configuration and the lumen pair configuration is configured to supply fluid to each of the two individual lumens such that each one of the at least two chambers of the inflatable balloon may be filled independently of the other.

13. The tissue dissector according to claim 1, wherein a distal end of the outer member is disposed proximal to the annular projection.

14. The tissue dissector according to claim 1, wherein the proximal portion of the outer member is connected to the elongated shaft proximal to the inflation port.

15. A system for electrosurgically treating tissue, comprising:
   a source of electrosurgical energy;
   an electrosurgical instrument adapted to operably couple to the source of electrosurgical energy and configured to electrosurgically treat target tissue; and
   a tissue dissector, comprising:
      a cannula having a longitudinal channel defined therethrough, the cannula having a notch defined along a length thereof; and
      an introducer coaxially coupleable to the cannula and movable therein between a retracted position and an extended position, the introducer including:
         an elongated shaft having a distal tip configured to pierce tissue;
         an outer member having a proximal portion connected to the elongated shaft and a distal portion disposed in spaced relation to the elongated shaft to define an annular lumen between the distal portion of the outer member and the elongated shaft, the annular lumen disposed in fluid communication with an inflation port operably disposed on the introducer and in fluid communication with an inflatable balloon, the inflatable balloon configured to couple to the distal portion of the outer member; and
         an annular projection disposed on a distal end of the introducer proximal to the distal tip and configured to be disposed within the longitudinal channel defined through the cannula and to engage a distal end of the longitudinal channel defined through the cannula to maintain the introducer in a fixed position relative to the cannula when the introducer is in the retracted position,
      wherein the inflatable balloon is movable between a deflated condition for positioning the introducer adjacent target tissue, and an inflated condition for separating the target tissue from nearby tissue and for providing a barrier therebetween.

* * * * *